United States Patent
Carling et al.

(10) Patent No.: US 6,593,325 B1
(45) Date of Patent: Jul. 15, 2003

(54) PYRIDO-PYRIDAZINE DERIVATIVES AS LIGANDS FOR GABA RECEPTORS

(75) Inventors: William Robert Carling, Bishops Stortford (GB); Jose Luis Castro Pineiro, Bishops Stortford (GB); Andrew Mitchinson, Sawbridgeworth (GB); Leslie Joseph Street, Little Hallinbury (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 10/069,379

(22) PCT Filed: Aug. 30, 2000

(86) PCT No.: PCT/GB00/03353

§ 371 (c)(1),
(2), (4) Date: Feb. 20, 2002

(87) PCT Pub. No.: WO01/18001

PCT Pub. Date: Mar. 15, 2001

(30) Foreign Application Priority Data

Sep. 9, 1999 (GB) .............................. 9921351

(51) Int. Cl.⁷ ............... A61K 31/5025; A61K 31/5377; C07D 487/04

(52) U.S. Cl. ................... 514/234.2; 514/248; 544/117; 544/236

(58) Field of Search ................ 544/236, 117; 514/248, 234.2

(56) References Cited

U.S. PATENT DOCUMENTS 6,103,903 A * 8/2000 Cai et al.

FOREIGN PATENT DOCUMENTS

| WO | WO 9804559 | 2/1998 |
| WO | WO 9965904 | 12/1999 |

* cited by examiner

*Primary Examiner*—Emily Bernhardt
(74) *Attorney, Agent, or Firm*—J. Eric Thies; Baerbel Brown; Melvin Winokur

(57) ABSTRACT

A class of pyrido[2,3-d]pyridazine derivatives, possessing an optionally substituted cycloalkyl, phenyl or heteroaryl substituent at the 8-position, a substituted alkoxy moiety at the 2-position, and a range of substituents at the 3-position, are selective ligands for $GABA_A$ receptors, in particular having high affinity for the $\alpha 2$ and/or $\alpha 3$ and/or $\alpha 5$ subunit thereof, and are accordingly of benefit in the treatment and/or prevention of adverse conditions of the central nervous system, including anxiety, convulsions and cognitive disorders.

9 Claims, No Drawings

PYRIDO-PYRIDAZINE DERIVATIVES AS LIGANDS FOR GABA RECEPTORS

This application is a U.S. National Phase application under 35 U.S.C. 371 of PCT Application No. PCT/GB00/03353, filed Aug. 30, 2000, which claims priority under 35 U.S.C. 119 from GB Application No. 9921351.4, filed Sep. 9, 1999.

BACKGROUND OF THE INVENTION

The present invention relates to a class of substituted pyrido-pyridazine derivatives and to their use in therapy. More particularly, this invention is concerned with substituted pyrido[2,3-d]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early state. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an al subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

SUMMARY OF THE INVENTION

The present invention provides a class of pyrido-pyridazine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

DETAILED DESCRIPTION OF THE INVENTION

The present invention provides a compound of formula I, or a salt or Prodrug thereof:

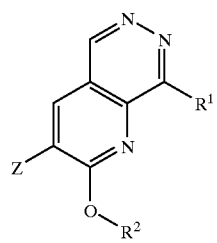

(I)

wherein

Z represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl or di($C_{1-6}$)alkylamino, any of which groups may be optionally substituted;

$R^1$ represents $C_{3-7}$ cycloalkyl, phenyl, furyl, thienyl or pyridinyl, any of which groups may be optionally substituted; and $R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

The groups Z, $R^1$ and $R^2$ may be unsubstituted, or substituted by one or more, suitably by one or two, substituents. In general, the groups Z, $R^1$ and $R^2$ will be unsubstituted or monosubstituted. Examples of optional substituents on the groups Z, $R^1$ and $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$)alkoxy. Particular substituents include methyl and fluoro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical $C_{6-8}$ bicycloalkyl groups include bicyclo[2.1.1]hexyl and bicyclo[2.2.1]heptyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible it vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, phenyl, pyrrolidinyl, methyl-pyrrolidinyl, piperidinyl, morpholinyl, thiomorpholinyl, pyridinyl, furyl, thienyl, chloro-thienyl and diethylamino.

In a particular embodiment, the substituent Z represents $C_{3-7}$ cycloalkyl, either unsubstituted or substituted by $C_{1-6}$ alkyl, especially methyl. Favourably, Z represents cyclobutyl.

In another embodiment, Z represents tert-butyl.

In a further embodiment, Z represents phenyl.

Examples of typical optional substituents on the group $R^1$ include methyl, fluoro and methoxy, especially fluoro.

Representative values of $R^1$ include cyclopropyl, phenyl, methylphenyl, fluorophenyl, difluorophenyl, methoxyphenyl, furyl, thienyl, methyl-thienyl and pyridinyl. More particularly, $R^1$ may represent unsubstituted, monosubstituted or disubstituted phenyl. Most particularly, $R^1$ represents phenyl, fluorophenyl or difluorophenyl, especially phenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^2$ represents an optionally substituted triazolylmethyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

A favoured value of $R^2$ is methyl-triazolylmethyl.

A particular sub-class of compounds according to the invention is represented by the compounds of formula IIA, and salts and prodrugs thereof:

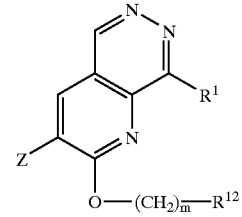

(IIA)

wherein

Z and $R^1$ are as defined with reference to formula I above;

m is 1 or 2, preferably 1; and $R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted by one or more substituents.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl.

Particular values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{12}$ is methyl-triazolyl.

A particular subset of the compounds of formula IIA above is represented by the compounds of formula IIB, and pharmaceutically acceptable salts thereof:

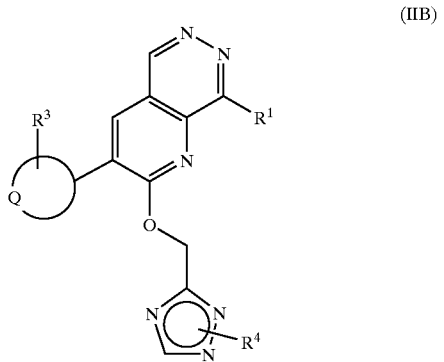

(IIB)

wherein
$R^1$ is as defined with reference to formula I above;
Q represents the residue of a cyclopropyl, cyclobutyl, cyclopentyl, cyclohexyl or phenyl ring;
$R^3$ represents hydrogen, methyl or fluoro; and
$R^4$ represents methyl or ethyl.

In relation to formula IIB above, $R^1$ suitably represents phenyl, fluorophenyl or difluorophenyl, especially phenyl.

In a particular embodiment, Q suitably represents the residue of a cyclobutyl ring. In another embodiment, Q represents the residue of a phenyl ring.

Suitably, $R^3$ represents hydrogen.
Suitably, $R^4$ represents methyl.

Specific compounds within the scope of the present invention include:
3,8-diphenyl-2-(2-methyl-2H-[1,2,4]triazol-3-ylmethoxy) pyrido[2,3-d]pyridazine;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychophamacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 21, 101–108.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III (or its 2-hydroxypyrido[2,3-d]pyridazine tautomer) with a compound of formula IV:

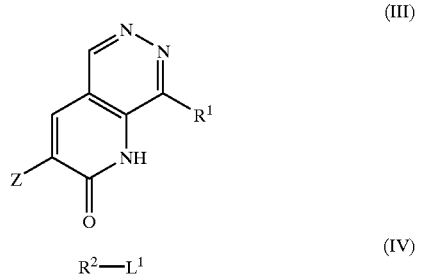

(III)

(IV)

wherein Z, R$^1$ and R$^2$ are as defined above, and L$^1$ represents a suitable leaving group.

The leaving group L$^1$ is suitably a halogen atom, typically chloro.

The reaction between compounds III and IV is conveniently effected by stirring the reactants in a suitable solvent, typically N,N-dimethylformamide, in the presence of a base such as cesium carbonate or potassium carbonate.

The intermediates of formula III above may be prepared by reacting a compound of formula V with a compound of formula VI:

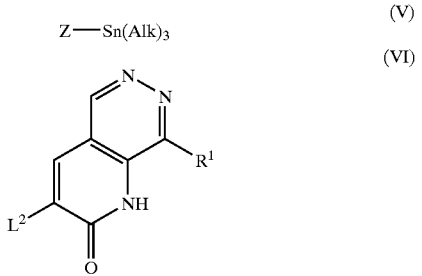

(V)

(VI)

wherein Z and R$^1$ are as defined above, L$^2$ represents a suitable leaving group, and Alk represents a $C_{1-6}$ alkyl group, typically n-butyl; in the presence of a transition metal catalyst.

The leaving group L$^2$ is suitably a halogen atom, e.g. bromo.

A suitable transition metal catalyst of use in the reaction between compounds V and VI is tris(dibenzylideneacetone)dipalladium(0), in which case the reaction is conveniently effected at an elevated temperature in a solvent such as N,N-dimethylformamide, typically in the presence of triphenylarsine.

The intermediates of formula IV above may be prepared by the procedures described in WO 98/04559, or by methods analogous thereto.

Where they are not commercially available, the starting materials of formula V and VI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein R$^2$ is unsubstituted may be converted into a corresponding compound wherein R$^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the R$^2$ substituent is substituted by a halogen atom, e.g. chloro, may be converted into the corresponding compound wherein the R$^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Example illustrates the preparation of compounds according to the invention.

The compounds in accordance with this invention potently inhibit the binding of [$^3$H]-flumazenil to the benzodiazepine binding site of human GABA$_A$ receptors containing the α2 or α3 or α5 subunit stably expressed in Ltk$^−$ cells.

The compound of the accompanying Example has been found to possess a K$_i$ value for displacement of [$^3$H]-flumazenil from the α2 and/or α3 and/or α5 subunit of the human GABA$_A$ receptor of 100 nM or less.

EXAMPLE 1

3,8-Diphenyl-2-(2-methyl-2H-[1,2,4]triazol-3-ylmethoxy)pyrido[2,3-d]pyridazine a) 2-Benzoyl-6-oxo-1,4,5,6-tetrahydropyridine-3-carboxylic acid methyl ester To diisopropylamine (6.05 ml) in THF (100 ml) at −78° C. under nitrogen was added n-butyllithium (26.6 ml of a 1.6

M solution in hexanes) dropwise. (2-Oxo-2-phenylethyl) carbamic acid tert-butyl ester (prepared according to the procedure of A. Guzman, C. Quintero and J. M. Muchowski; *Can. J. Chem.*, 1991, 69, 2059–63) (10.0 g) in THF (50 ml) was added dropwise to the resultant solution, maintaining the temperature of the reaction mixture at <−60° C. throughout the addition. The deep red-brown solution was stirred at −78° C. for 30 min, then dimethyl 2-ketoglutarate (prepared according to the procedure of D. L. J. Clive, D. M. Coltart and Y. Zhou, *J. Org. Chem.*, 1999, 64, 1447–54) (8.14 g) in THF (50 ml) was added dropwise, maintaining the temperature as before. The pale orange solution was stirred at −78° C. for 5 h, then saturated ammonium chloride solution (100 ml) was added. The mixture was allowed to warm to room temperature, and was filtered to remove insoluble material. The aqueous phase of the filtrate was washed with dichloromethane (2×50 ml), then the washings were combined with the organic phase and washed with water (1×50 ml), dried over magnesium sulfate and were then concentrated in vacuo. The residue was purified by flash chromatography on sica gel, eluting with 25% ethyl acetate in isohexane, yielding a white solid (8.63 g). This material was stirred in trifluoroacetic acid (170 ml) at room temperature for 10 min, and was then concentrated in vacuo. The residue was dissolved in dichloromethane (600 ml), and triethylamine (8.82 ml) was added. The solution was stirred at room temperature overnight, was washed with water (1×250 ml) and dried over magnesium sulfate, and was then concentrated in vacuo. The residual oil was purified by flash chromatography on silica gel, eluting with 0 to 5% methanol in dichloromethane, yielding an orange gum (3.45 g). This was heated at reflux in trifluoroacetic acid (50 ml) for 4 days. The solvent was removed in vacuo, and the residue was purified by flash chromatography on silica gel, eluting with 0 to 3% methanol in dichloromethane, yielding 2-benzoyl-6-oxo-1,4,5,6-tetrahydropyridine-3-carboxylic acid methyl ester as a dark brown oil (3.24 g). $^1$H NMR (400 MHz, CDCl$_3$) δ2.68 (2H, t, J=8.1 Hz), 2.86 (2H, t, J=8.0 Hz), 3.39 (3H, s), 7.31 (1H, br s), 7.50 (2H, t, J=7.7 Hz), 7.63 (1H, t, J=7.4 Hz), 7.89 (2H, d, J=7.7 Hz); MS (ES$^+$) m/e 260 [MH]$^+$, 228 [M−OMe]$^+$, 186.

b) 2-Benzoyl-6-oxo-1,6-dihydropyridine-3-carboxylic acid methyl ester

2-Benzoyl-6-oxo-1,4,5,6-tetrahydropyridine-3-carboxylic acid methyl ester (5.97 g) and 2,3-dichloro-5,6-dicyano-1,4-benzoquinone (DDQ, 7.85 g) were stirred together at reflux in toluene (125 ml) for 24 h. More DDQ (7.85 g) was added and the mixture was stirred as before for a further 24 h. The solvent was removed in vacuo, and the residue was purified by flash chromatography on silica gel, eluting with 1:1 ethyl acetate:isohexane, yielding 2-benzoyl-6-oxo-1,6-dihydropyridine-3-carboxylic acid methyl ester as a brown solid (2.07 g). $^1$H NMR (400 MHz, CDCl$_3$) δ3.54 (3H, s), 6.60 (1H, d, J=9.7 Hz), 7.50 (2H, t, J=7.8 Hz), 7.64 (1H, t, J=7.4 Hz), 7.82 (2H, d, J=8.2 Hz), 7.95 (1H, d, J=9.7 Hz), 11.00 (1H, br s); MS (ES$^+$) m/e 258 [MH]$^+$, 226 [M−OMe]$^+$.

c) 2-Benzoyl-6-benzyloxynicotinic acid methyl ester

A slurry of 2-benzoyl-6-oxo-1,6-dihydropyridine-3-carboxylic acid methyl ester (1.00 g), benzyl bromide (1.88 ml) and silver carbonate (1.64 g) in toluene (50 ml) was stirred at room temperature in the dark under nitrogen for 3 days. More silver carbonate (0.82 g) was added and the slurry was stirred as before for 24 h. A final portion of silver carbonate (0.82 g) was added, and the mixture was stirred as before for 3 days. The mixture was filtered, and the filtrate was concentrated in vacuo. The residue was purified by flash chromatography on silica gel, eluting with dichloromethane, yielding 2-benzoyl-6-benzyloxynicotinic acid methyl ester as a pale brown solid (1.14 g). $^1$H NMR (400 MHz, CDCl$_3$) δ3.69 (3H, s), 5.39 (2H, s), 6.92 (1H, d, J=8.8 Hz), 7.30 (3H, m), 7.37 (2H, m), 7.45 (2H, t, J=7.7 Hz), 7.59 (1H, t, J=7.4 Hz), 7.78 (2H, d, J=7.8 Hz), 8.25 (1H, d, J=8.7 Hz); MS (ES$^+$) m/e 348 [MH]$^+$.

d) 2-Benzyloxy-8-phenyl-6H-pyrido[2,3-d]pridazin-5-one

2-Benzoyl-6-benzyloxynicotinic acid methyl ester (1.14 g) and hydrazine monohydrate (0.40 ml) were stirred together in ethanol (50 ml) at reflux overnight. The reaction was cooled (ice bath) precipitating a solid, which was separated by filtration and washed with diethyl ether. This was 2-benzyloxy-8-phenyl-6H-pyrido[2,3-d]pridazin-5-one (0.845 g). $^1$H NMR (400 MHz, DMSO) δ5.42 (2H, s), 7.33 (6H, m), 7.50 (3H, m), 7.86 (2H, m), 8.51 (1H, d, J=9.7 Hz), 13.04 (1H, s); MS (ES$^+$) m/e 330 [MH]$^+$.

e) 2-Benzyloxy-5-chloro-8-phenylpyrido[2,3-d]pyridazine

2-Benzyloxy-8-phenyl-6H-pyrido[2,3-d]pridazin-5-one (845 mg) was stirred in phosphorus oxychloride (30 ml) at reflux for 4 h. The solvent was removed in vacuo and the residue was purified by flash chromatography on silica gel, eluting with ethyl acetate, yielding 2-benzyloxy-5-chloro-8-phenylpyrido[2,3-d]pyridazine as a pale yellow solid (950 mg). $^1$H NMR (400 MHz, DMSO) δ5.50 (2H, s), 7.35 (5H, m), 7.58 (3H, m), 7.65 (1H, d, J=9.0 Hz), 8.06 (2H, m), 8.60 (1H, d, J=9.0 Hz); MS (ES$^+$) m/e 348, 350 [MH]$^+$.

f) 8-Phenyl-1H-pyrido[2,3-d]pyridazin-2-one

2-Benzyloxy-5-chloro-8-phenylpyrido[2,3-d]pyridazine (250 mg), ammonium formate (115 mg) and 10% palladium on carbon catalyst (50 mg) were stirred together at reflux in propan-2-ol (50 ml) for 30 min. More ammonium formate (45 mg) was added, and the mixture was stirred as before for a further 30 min, and was then allowed to cool to room temperature. The catalyst was removed by filtration, was washed thoroughly with methanol, and the filtrate was concentrated in vacuo to yield 8-phenyl-1H-pyrido[2,3-d]pyridazin-2-one as a white solid (150 mg). $^1$H NMR (400 MHz, CDCl$_3$) δ6.98 (1H, d, J=9.4 Hz), 7.63 (3H, m), 7.69 (2H, m), 7.85 (1H, d, J=9.5 Hz), 8.88 (1H, br s), 9.23 (1H, s); MS (ES$^+$) m/e 224 [MH]$^+$.

g) 3-Bromo-8-phenyl-1H-pyrido[2,3-d]pyridazin-2-one

8-Phenyl-1H-pyrido[2,3-d]pyridazin-2-one (46 mg) and bromine (0.11 ml) were stirred together in acetic acid (3 ml) at 90° C. for 7 days, adding a fresh aliquot of bromine (0.11 ml) every 24 h. The mixture was allowed to cool to room temperature, precipitating a solid. This was separated by filtration and purified by flash chromatography on silica gel, eluting with 1:1 ethyl acetate:isohexane, then 100% ethyl acetate, yielding 3-bromo-8-phenyl-1H-pyrido[2,3-d]pyridazin-2-one as a pale yellow solid (10 mg). $^1$H NMR (400 MHz, CDCl$_3$) δ7.67 (5H, m), 8.29 (1H, s), 9.02 (1H, br s), 9.21 (1H, s); MS (ES$^+$) m/e 302, 304 [MH]$^+$.

h) 3,8-Diphenyl-1H-pyrido[2.3-d]pyridazin-2-one

3-Bromo-8-phenyl-1H-pyrido[2,3-d]pyridazin-2-one (80 mg), tris(dibenzylideneacetone)dipalladium(0) (11 mg) and triphenylarsine (14 mg) were stirred together in DMF (20 ml) at room temperature with nitrogen bubbling through the solution for 15 min. Tributylphenyltin (91 μl) was added, and the mixture was stirred at 80° C. under nitrogen for 90 min. The solution was allowed to cool to room temperature and concentrated in vacuo. The residue was purified by flash chromatography on silica gel, eluting with 25 to 50% ethyl acetate in dichloromethane, yielding 3,8-diphenyl-1H-pyrido[2,3-d]pyridazin-2-one as a white solid (50 mg). $^1$H NMR (400 MHz, CDCl$_3$) δ7.48 (3H, m), 7.65 (3H, m), 7.74 (4H, m), 7.93 (1H, s), 9.99 (1H, br s), 9.28 (1H, s); MS (ES$^+$) m/e 300 [MH]$^+$.

i) 3,8-Diphenyl-2-(2-methyl-2H-[1,2,4]triazol-3-ylmethoxy)(pyrido[2,3-d]pyridazine 3,8-Diphenyl-1H-pyrido[2,3-d]pyridazin-2-one (40 mg), cesium carbonate (174 mg) and 3-(chloromethyl)-2-methyl-2H-[1,2,4]triazole (prepared using the conditions described in EP-A-0170073) (27 mg) were stirred together at room temperature in DMF (4 ml) under nitrogen overnight. Water (25 ml) was added and the resultant solution was washed with dichloromethane (3×25 ml). The combined organic washings were dried over magnesium sulfate and concentrated in vacuo. The residue was purified by preparative thin layer chromatography on silica gel, eluting with 5% methanol in dichloromethane. The product was recrystallised froim diethyl ether/ethanol/ethyl acetate, yielding 3,8-diphenyl-2-(2-methyl-2H-[1,2,4]triazol-3-ylmethoxy)pyrido[2,3-d]pyridazine as a white solid (8 mg). Data for the title compound: m.p. 222–223° C. $^1$H NMR (400 MHz, CDCl$_3$) δ3.62 (3H, s), 5.67 (2H, s), 7.48 (3H, m), 7.56 (3H, m), 7.63 (2H, m), 7.85 (1H, s), 8.13 (2H, m), 8.20 (1H, s), 9.49 (1H, s); MS (ES$^+$) m/e 395 [MH]$^+$.

What is claimed is:

1. A compound of formula IIB, or a pharmaceutically acceptable salt thereof:

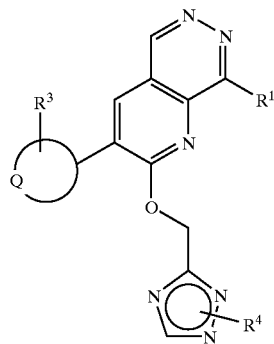

(IIB)

wherein

Q represents the residue of a cyclopropyl, cyclobutyl, cyclopentyl, cyclohexyl or phenyl ring;

R$^1$ represents C$_{3-7}$ cycloalkyl, phenyl, furyl, thienyl or pyridinyl, any of which groups may be unsubstituted or substituted with one or more substituents selected from the group consisting of C$_{1-6}$ alkyl, aryl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, C$_{1-6}$ alkoxy, C$_{3-7}$ cycloalkyl(C$_{1-6}$)alkoxy, C$_{3-7}$ cycloalkoxy, anino(C$_{1-6}$)alkyl, di(C$_{1-6}$)alkylamino(C$_{1-6}$)alkyl, di(Ci) alkylaminocarbonyl(C$_{1-6}$)alkyl, N-(C$_{1-6}$) alkylpiperidinyl, pyrrolidinyl(C$_{1-6}$)alkyl, piperazinyl (C$_{1-6}$)alkyl, morpholinyl(C$_{1-6}$)alkyl, di(C$_{1-6}$) alkylmorpholinyl(C$_{1-6}$)alkyl and imidazolyl(C$_{1-6}$) alkyl;

R$^3$ represents hydrogen, methyl or fluoro; and

R$^4$ represents methyl or ethyl.

2. The compound of claim 1 wherein Q represents the residue of a phenyl ring.

3. The compound of claim 1 wherein R$^1$ represents phenyl, fluorophenyl or difluorophenyl.

4. A compound selected from:

3,8-diphenyl-2-(2-methyl-2H-[1,2,4]triazol-3-ylmethoxy) pyrido[2,3d]pyridazine; or a pharmaceutically acceptable salt thereof.

5. A pharmaceutical composition comprising the compound of claim 1 or a pharmaceutically acceptable salt thereof and a pharmaceutically acceptable carrier.

6. A method for the treatment of anxiety which comprises administering to a patient in need of such treatment an effective amount of the compound of claim 1 or a pharmaceutically acceptable salt thereof.

7. A method for the prevention of anxiety which comprises administering to a patient in need of such treatment an effective amount of the compound of claim 1 or a pharmaceutically acceptable salt thereof.

8. A method for the treatment of convulsions which comprises administering to a patient in need of such treatment an effective amount of the compound of claim 1 or a pharmaceutically acceptable salt thereof.

9. A method for the prevention of convulsions which comprises administering to a patient in need of such treatment an effective amount of the compound of claim 1 or a pharmaceutically acceptable salt thereof.

* * * * *